(12) United States Patent
Furuta

(10) Patent No.: US 6,905,839 B2
(45) Date of Patent: Jun. 14, 2005

(54) IN VIVO PHENOTYPING FOR HUMAN CYTOCHROME P450 3A ACTIVITY

(76) Inventor: Takashi Furuta, 2-22-10 Komoa-Shiotsu, Uenohara-machi, Kitatsuru-gun, Yamanashi-ken 409-0126 (JP)

( * ) Notice: Subject to any disclaimer, the term of this patent is extended or adjusted under 35 U.S.C. 154(b) by 344 days.

(21) Appl. No.: 10/209,459

(22) Filed: Jul. 31, 2002

(65) Prior Publication Data

US 2004/0022728 A1 Feb. 5, 2004

(51) Int. Cl.[7] ............................. C12Q 1/02; C12Q 1/34; C12Q 1/00
(52) U.S. Cl. ................... 435/29; 435/18; 435/4
(58) Field of Search .................. 435/29, 18, 4

(56) References Cited

U.S. PATENT DOCUMENTS

| | | | |
|---|---|---|---|
| 5,567,592 A | * 10/1996 | Benet et al. | ............. 435/7.21 |
| 2004/0022728 A1 | * 2/2004 | Furuta | ............. 424/9.1 |

OTHER PUBLICATIONS

Ohno et al; J. of Chromatography. B, Biomedical sciences and applications; V. 746(1);pp. 95–101; Sep. 1, 2000.*
Wilkinson, G.R.; J. Pharmacokinetics and biopharmaceutics; V. 24(5); pp475–90; Oct. 1996; (Abstract Only).□□.*
Keung et al; Int. J. Tuberc. Lung Dis; V. 3(5); p 426–36;May 1999; (Abstract Only).*
Kinirons et al., Clin. Pharmacol. Ther., vol. 54, 621–9 (1993).
Bienvenu et al., Int. J. Clin. Pharmacol. Ther. Toxicol., vol. 29, 441–5 (1991).
Streetman et al., Pharmacogenetics, vol. 10, 187–216 (2000).
Y.S. Lin et al., Pharmacogenetics, vol. 11, No. 9, 781–791 (2001).
K.S. Lown et al., Clinical Pharmacology & Therapeutics, vol. 57, No. 1, 16–24 (Jan. 1995).
C. Ged et al., Br. J. Clin. Pharmac., vol. 28, 373–387 (1989).
P. Watkins et al., Clin. Pharmacol. Ther., vol. 52, No. 3, 265–273 (1992).
S.L. Eeckhoudt et al., Int'l. J. Clin. Pharmocology and Therapeutics, vol. 39, No. 7, 293–299 (2001).
T. Furuta et al., Drug Metabolism and Deposition, vol. 24, No. 1, 49–54 (1996).
Clinical Pharmacology & Therapeutics, vol. 71, No. 1, 33–43 (Jul. 2002).
Xenobiotic Metabolism and Disposition, vol. 16, Supplement, 98–99 (Sep. 17, 2001) in Japanese with an English translation.

* cited by examiner

*Primary Examiner*—Louise N. Leary
(74) *Attorney, Agent, or Firm*—Ohlandt, Greeley, Ruggiero & Perle, LLP; George W. Rauchfuss, Jr.

(57) ABSTRACT

In a method for evaluating in vivo human cytochrome P450 3A (CYP3A), at least a 2-hour urine collection and one blood sample are obtained. Endogenous cortisol in plasma and 6β-hydroxycortisol in urine are measured. Metabolic clearance specific for the 6β-hydroxylation of cortisol is then expressed as the amount of urinary excreted 6β-hydroxycortisol divided by the area under the concentration-time curve of cortisol, being a safe and reliable index for CYP3A phenotyping to assess in vivo CYP3A activity in humans.

12 Claims, 2 Drawing Sheets

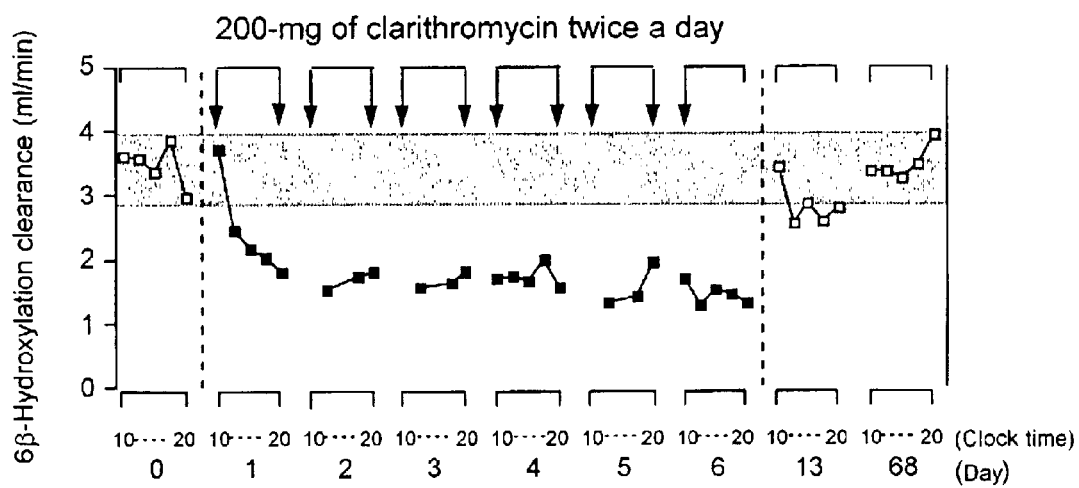
FIG. 3 (Predose)
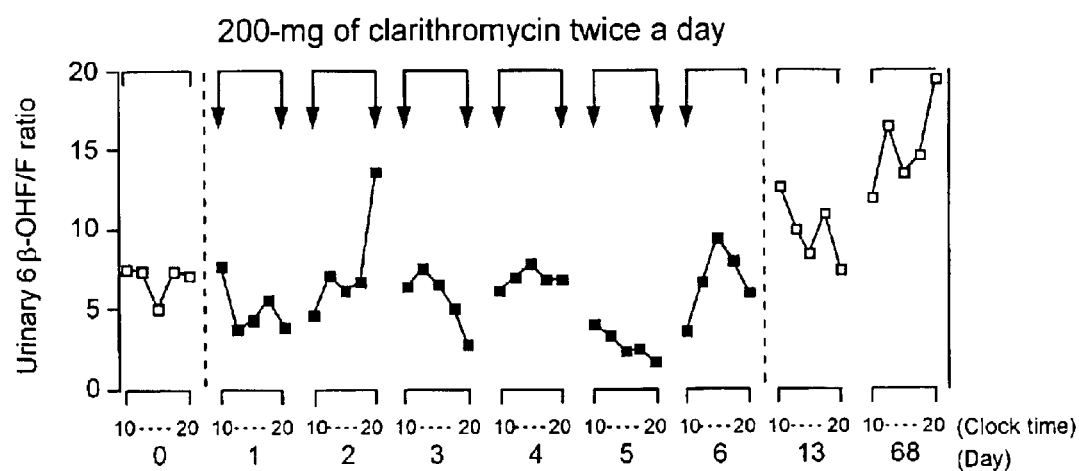
FIG. 4 (Predose)
(Prior Art)

IN VIVO PHENOTYPING FOR HUMAN CYTOCHROME P450 3A ACTIVITY

FIELDS OF THE INVENTION

This invention relates to methods of evaluating human cytochrome P450 3A (CYP3A) activity in vivo, which can be used for predicting or assessing the metabolic capacity of CYP3A substrate drugs. The invention is useful for and involved in the fields of drug development and clinical research and practice.

BACKGROUND OF THE INVENTION

Cytochrome P450 (CYP) constitutes a multigene family of hemoproteins responsible for the metabolism of numerous xenobiotics including therapeutic drugs, environmental chemicals, and dietary constitutes, as well as endogenous substrates such as steroids and bile acids. Among the human CYP proteins, CYP3A is the most abundant cytochrome P450 isozyme and plays an important role in the oxidative metabolism of a number of widely used and clinically important drugs. It is estimated that approximately 50% of all currently used drugs are substrates for CYP3A, including steroids, HIV protease inhibitors, benzodiazepines, calcium channel blockers, cholesterol-lowering drugs, immunosuppressants, cancer chemotherapeutics, macrolide antibiotics, etc.

A marked interindividual variability of the catalytic function to metabolize CYP3A substrates has been demonstrated, exceeding 20-fold in some populations. The variability of CYP3A activity is assumed to reflect the combined effects of genetic and environmental factors. CYP3A activity can be readily modulated by inducers (e.g., rifampicin and anticonvulsant agents), and many potent inhibitors (e.g., azole antifungal agents and macrolide antibiotics). Metabolism involving CYP3A is also affected by liver disease, aging, gender, race, etc. Variation in CYP3A activity is particularly important for substrates with narrow therapeutic indices, such as cancer chemotherapeutics and immunosuppressants. The term "CYP3A-phenotyping" may be defined as an assessment of the CYP3A in vivo activity to metabolize a specific CYP3A substrate (whether it is endogenous or exogenous) in a subject in a certain state, condition, time, etc. CYP3A-Phenotyping in a human subject provides valuable information about actual and real-time enzyme activity in vivo to metabolize the substrate, which can allow prediction or assessment of his or her ability for metabolizing other CYP3A substrates as well. Hence, it can allow individualization of dosing of a certain CYP3A substrate drugs. Also, inadequate dosing can be avoided thereby. The phenotyping is also becoming an important aspect of drug development for predicting the potential inhibition or induction of CYP3A enzyme caused by new drugs (drug-drug interactions). Knowledge of the role of CYP3A in the metabolism of a putative drug candidate are desirable at an early stage in the drug development process, for assisting in the choice of the best drug candidate for further development.

PRIOR ART

Several CYP3A substrates have been evaluated as potential in vivo probes, including erythromycin, midazolam, cortisol, etc. However, much controversy regarding the selection of an ideal CYP3A probe remains. See, for example, Kinirons, M. T. et al., "Absence of correlations among three putative in vivo probes of human cytochrome P4503A activity in young healthy men." Clin. Pharmacol. Ther., vol. 54, 621–9 (1993); and Streetman, D. S. et al., "Phenotyping of drug-metabolizing enzymes in adults: a review of in-vivo cytochrome P450 phenotyping probes." Pharmacogenetics, vol. 10, 187–216 (2000). To perform the erythromycin breath test, a subject receives an intravenous injection of radioactive N-[$^{14}$C-methyl]-erythromycin. This test is relatively simple and fast, but there is significant day-to-day variability, as well as discrepancies between the erythromycin breath test and the disposition of several CYP3A substrates. The erythromycin breath test also has several practical disadvantages including exposure to radioactivity, intravenous administration of drug, and the need for a period of supervised study. Midazolam, which undergoes CYP3A-catalyzed hydroxylation, is now considered to have some advantage over the erythromycin breath test and other probes for determining CYP3A activity. Total clearance of midazolam is used as an in vivo marker of hepatic and intestinal CYP3A phenotype following oral and intravenous administration, respectively. The method requires a pharmacological dose of midazolam, producing transient sedation and memory impairment in some subjects. The test also involves multiple blood sampling over a prolonged interval and the analytical techniques involved are relatively complex for accurately determining total clearance of midazolam following oral or intravenous administration.

The 6β-hydroxylation of cortisol, an endogenous compound, is mediated by CYP3A isozyme. Therefore, the urinary ratio of 6β-hydroxycortisol to cortisol (6β-hydroxycortisol/cortisol) has been measured extensively as a useful non-invasive index for the enzyme activity in vivo to evaluate drug-drug interactions (inductions and inhibitions), involving the CYP3A isozyme in patients undergoing therapies with multiple drugs. The urinary ratio has also been used for the elucidation of the statistical correlation of CYP3A activity with genetic and/or environmental factors in different populations, regarding disease states, age, ethnic differences, etc. See, for example, Bienvenu, T. et al., "A simple non-invasive procedure for the investigation of cytochrome P-450 IIIA dependent enzymes in humans," Int. J. Clin. Pharmacol. Ther. Toxicol., vol. 29, 441–5 (1991); and Streetman, D. S. et al., "Phenotyping of drug-metabolizing enzymes in adults: a review of in-vivo cytochrome P450 phenotyping probes." Pharmacogenetics, vol. 10, 187–216 (2000). In spite of numerous studies describing success and validations of the urinary 6β-hydroxycortisol/cortisol ratio, the marker does not always provide results similar to those of the CYP3A-mediated oxidation in vivo after administrating a probe drug such as erythromycin and midazolam or other CYP3A substrates. The exact reasons of lacking expected correlations between urinary excretion of 6β-hydroxylcortisol and in vivo metabolism of other probes still remain obscure.

OBJECT OF THE INVENTION

Because of wide interindividual variations in the CYP3A activity in humans, the development of in vivo CYP3A phenotyping by using specific probe drugs has been the subjects for simply and accurately predicting the CYP3A-metabolizing capacity of an individual or comparing this enzyme activity among different populations in the fields of drug development and clinical research and practice. Genetic polymorphisms have also been described for most drug-metabolizing enzymes such as CYP1A2, CYP2C19, CYP2D6, CYP3A, etc., but the functional importance of genetic variability in CYP3A remains unclear. The recent discovery of genetic polymorphisms in the CYP3A4 and CYP3A5 genes (P. Kuehl, et al., (2001) Nature Genetics, 27, pp 383–391., and F.-C. Chou, et al., (2001) Drug. Metab. Dispos., 29, pp 1205–1209.) has increasingly required a safe and reliable method of CYP3A phenotyping to support the identification of important genetic polymorphisms that affect CYP3A expression.

Even though metabolism of cortisol to 6β-hydroxylcortisol is known to be mediated by CYP3A isozyme, and urinary 6β-hydroxycortisol/cortisol ratio has been actually used (with questionable reliability) as an index of CYP3A activity as described above, simple and non-invasive and yet reliable method for estimating CYP3A activity has never been so far known or suggested. Thus, there is a need for developing a new method for estimating CYP3A activity which is simple, non-invasive and yet reliable.

On the other hand, metabolic clearance of endogenous 6β-hydroxylation of cortisol has never been suggested for estimation of CYP3A activity perhaps because cortisol is produced and metabolized in various pathways in a human body, and the excreted 6β-hydroxycortisol metabolite constitutes only approximately 1% of the total daily cortisol secretion, and such adrenal cortisol secretion has been thought to disturb the accurate determination of the elimination clearance of cortisol.

The present invention is primarily directed towards the development of a new and reliable method for phenotyping in vivo CYP3A activity in humans without employing exogenously administered substances as probes.

SUMMARY OF THE INVENTION

The present invention relates to methods for in vivo CYP3A phenotyping in humans. Metabolic clearance specific for the 6β-hydroxylation of endogenous cortisol is employed as the index for the phenotyping. A timed urine collection and one blood sample during a period of the urine collection (e.g., 2-hour) are obtained. (Each of the urine collection periods is started by asking the subjects to empty their urinary bladders.) Endogenous cortisol in plasma or serum and 6β-hydroxycortisol in urine are measured. (Cortisol amounts are substantially the same in plasma and in serum obtained from a given volume of blood.) Metabolic clearance for the 6β-hydroxylation is then expressed as the amount of urinary excreted 6β-hydroxycortisol divided by the area under the concentration-time curve of cortisol.

BRIEF DESCRIPTION OF THE DRAWINGS

FIG. 3 illustrates inhibitory effects of a macrolide antibiotic clarithromycin on the in vivo CYP3A activity evaluated by the present CYP3A-phenotyping using the endogenous 6β-hydroxylation clearance ($CLm_{(6\beta)-endo}$) in a human subject (Subject D) following administration of 200-mg of clarithromycin every 12 hr at 10:00 and 22:00 for 6 days (days 1–6).

FIG. 4 illustrates inhibitory effects of a macrolide antibiotic clarithromycin on the in vivo CYP3A activity evaluated by a conventional method using the urinary endogenous 6β-hydroxycortisol/cortisol ratio in a human subject (Subject D) following administration of 200-mg of clarithromycin every 12 hr at 10:00 and 22:00 for 6 days (days 1–6).

DETAILED DESCRIPTION OF THE INVENTION

Figure 1:
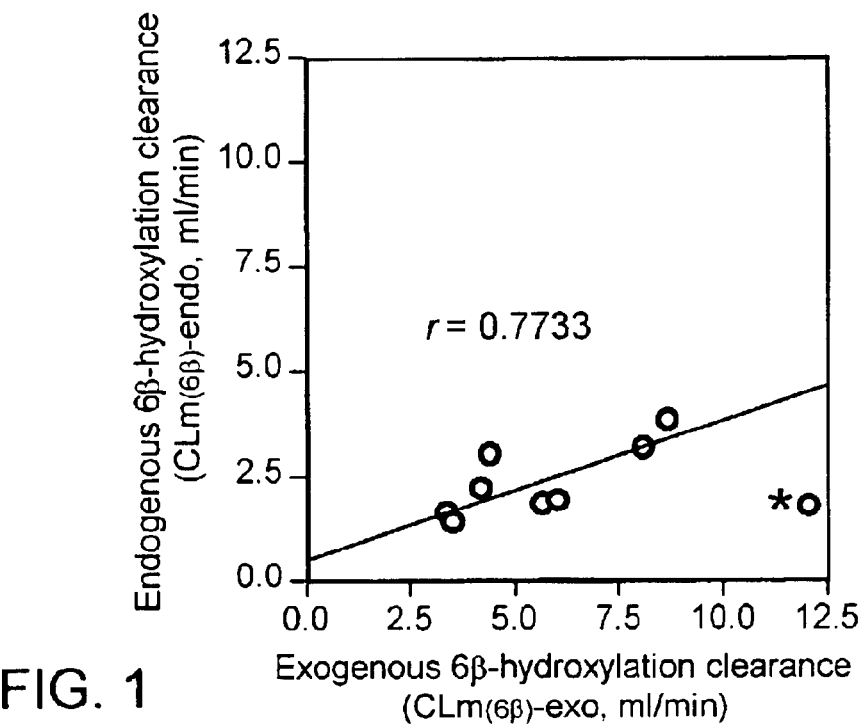
FIG. 1 illustrates the relationship between endogenous metabolic clearance ($CLm_{(6\beta)-endo}$) for the 6β-hydroxylation of cortisol versus exogenous metabolic clearance ($CLm_{(6\beta)-exo}$) for the 6β-hydroxylation of labeled cortisol after administrating stable isotopically labeled cortisol to three subjects, showing a good correlation (r=0.7733, P<0.005) between $CLm_{(6\beta)-endo}$ and $CLm_{(6\beta)-exo}$ obtained at timed periods of 10:00–12:00, 12:00–14:00, and 14:00–16:00 for Subjects A and C and of 10:00–12:00, 12:00–14:00, and 14:00–18:00 for Subject B. The plot shown by star symbol in FIG. 1 was excluded from the analysis for the regression curve.

In phenotyping by using a probe drug, the elimination clearance of the prove drug should provide the best estimate of the in vivo catalytic activity of the enzyme of interest (P. B. Watkins, (1994) Pharmacogenetics, 4, pp 171–184.). If the probe drug has multiple metabolic pathways, the fractional metabolic clearance corresponding to the pathway of interest should be an appropriate measure. In general, pharmacokinetic parameters such as metabolic and renal clearances of a drug are determined by measuring a series of concentrations of the parent drug and/or its metabolites in plasma and urine after administrating the drug. However, cortisol cannot be administered to human subjects for determining the pharmacokinetic parameters, since cortisol and its metabolites are already present as endogenous substances in human body. That is, endogenous cortisol secretes from the adrenal cortex and appears in the general circulation with seven or more major episodes throughout the day. Therefore, administration of stable isotopically labeled cortisol to human subjects should be the best way for accurately determining their metabolic clearances specific for the 6β-hydroxylation of cortisol catalyzed by CYP3A enzyme in vivo, since exogenously administered unlabeled cortisol is not exclusively measurable, being differentiated from endogenous one.

Stable isotope methodology has widely been accepted for investigating the pharmacokinetics and in vivo metabolism of endogenous substances such as steroids and amino acids in humans (T. A. Baillie, (1981) Pharmacological Reviews, 33, pp 81–132.). This method is based on the idea that the exogenously administered labeled compound as tracer after entering the general circulation distributes to tissues and is metabolized and excreted in an identical fashion to its endogenous couterpart compound. One of the major advantages of this methodology coupled with mass spectrometry is that endogenous and exogenous (labeled) compounds with the same basic structure can be differentiated easily by using the stable isotopically labeled compound as biological internal standard. The use of labeled cortisol for administration as the biological internal standard offers reliable informations concerning the pharmacokinetics and in vivo metabolism of cortisol in humans, since it does not involve the process of adrenal cortisol secretion that disturbs the accurate determination of the elimination clearance of cortisol.

This invention was first undertaken to determine fractional metabolic clearance specific for the 6β-hydroxylation of cortisol ($CLm_{(6\beta)-exo}$) by administrating stable isotopically labeled cortisol to human subjects in order to accurately evaluate the in vivo cytochrome P450 3A (CYP3A) activity. The obtained pharmacokinetic parameters such as metabolic and renal clearances of labeled cortisol were used as the reference standard for evaluating the validity of the following two endogenous indices for phenotyping in vivo human CYP3A activity: (1) the urinary ratio of endogenous 6β-hydroxycortisol/cortisol as a conventional index and (2) metabolic clearance for the 6β-hydroxylation of endogenous cortisol as a new index.

the amount of urinary excreted 6β-hydroxycortisol $(X_{(6\beta)-exo})$ divided by the area under the concentration-time curve of cortisol $(AUC_{(F)-exo})$:

$$CLm_{(6\beta)-exo} = X_{(6\beta)-exo}/AUC_{(F)-exo} \qquad [1]$$

The values of $CLm_{(6\beta)-exo}$, not being involved in the process of adrenal cortisol secretion that disturbs the accurate determination of the elimination clearance of cortisol as stated above, should be considered as a reliable index to show CYP3A activity.

TABLE I

| Subject | Clock time | CLm (6 β)-exo (ml/min) | X(6β)-exo / X(F)-exo | CLr (F)-exo (ml/min) |
|---|---|---|---|---|
| A | 10:00~16:00 | 8.77[a] | 3.94[a] | 2.23[a] |
|   |   | (8.69, 8.11, 12.0)[b] | (3.05, 13.0, 18.4)[b] | (2.85, 0.62, 0.65)[b] |
| B | 10:00~18:00 | 3.94[a] | 8.71[a] | 0.45[a] |
|   |   | (4.22, 3.57, 3.39)[b] | (6.96, 15.6, 20.1)[b] | (0.61, 0.23, 0.17)[b] |
| C | 10:00~16:00 | 4.75[a] | 6.31[a] | 0.75[a] |
|   |   | (4.48, 5.66, 6.10)[b] | (5.47, 14.0, 7.56)[b] | (0.82, 0.40, 0.81)[b] |

[a]The respective value for CLm(6β)-exo, X(6β)-exo/X(F)-exo, and CLr(F)-exo was calculated, based on the sum of each measured amount of labeled cortisol (in plasma and urine) or labeled 6β-hydroxycortisol (in urine) obtained at periods of 10:00~12:00, 12:00~14:00, and 14:00~16:00 (18:00). [b]The three values in each parentheses are shown in order of the following periods: 10:00~12:00, 12:00~14:00, and 14:00–16:00 (18:00).

Three healthy male volunteers (23–25 years old) received a single oral dose of either 5-mg cortisol-$d_5$ ([1,1,19,19,19-$^2$H$_5$]cortisol) for Subjects A and B or 3-mg cortisol-$^{13}$C$_4$ ([1,2,4,19-$^{13}$C$_4$]cortisol) for Subject C (T. Furuta, et al., (2000) Steroids, 65, pp 180–189.). Blood samples were obtained before and during a period of 8 h after dosing at 10:00 a.m. Urine samples were collected at timed periods (0–2, 2–4, 4–6 and 6–8 h for Subjects A and C and 0–2, 2–4 and 4–8 h for Subject B). Plasma concentrations of cortisol and urinary excreted amounts of cortisol and 6β-hydroxycortisol (unconjugated form) were analyzed by stable isotope dilution mass spectrometric method simultaneously with their exogenous labeled counterparts (T. Furuta, et al., (2000) J. Chromatogr. B., 738, pp 119–127., and T. Furuta, et al., (2000) J. Chromatogr. B., 738, pp 367–376.).

(1) Determination of Metabolic Clearance Specific for the 6β-Hydroxylation of Cortisol for use as a Reference Standard for Evaluating the In Vivo CYP3A Activity in Human: (Administration of Stable Isotopically Labeled Cortisol)

Cortisol is extensively metabolized through multiple metabolic pathways. The metabolite, 6β-hydroxycortisol, is excreted as unconjugated form in urine, and constitutes approximately 1% of the total daily cortisol secretion. Namely, metabolism by CYP3A isozyme is only a fraction of the total elimination of cortisol from the human body. The fractional metabolic clearance for the 6β-hydroxylation of exogenous (labeled) cortisol $(CLm_{(6\beta)-exo})$ after administrating stable isotopically labeled cortisol can be expressed as As shown in Table I, the $CLm_{(6\beta)-exo}$ values for a test period of 6 h or 8 h after administrating labeled cortisol were 8.77 ml/min (Subject A), 3.94 ml/min (Subject B), and 4.75 ml/min (Subject C), indicating the order of A>C>B in the CYP3A activity. The urinary 6βhydroxycortisol/cortisol ratios $(=X_{(6\beta)-exo}/X_{(F)-exo})$ at the same period were 3.94 (Subject A), 8.71 (Subject B) and 6.31 (Subject C), respectively (Table I). The order of B>C>A in the urinary 6β-hydroxycortisol/cortisol ratio $(=X_{(6\beta)-exo}/X_{(F)-exo})$ was not consistent with that (A>C>B) for the CYP3A activity.

Transforming Equation 1 into Equation 2, as indicated below, showed that the urinary 6β-hydroxycortisol/cortisol ratio $(=X_{(6\beta)-exo}/X_{(F)-exo})$ is a function of metabolic clearance for the 6β-hydroxylation $(CLm_{(6\beta)-exo})$ and renal clearance of cortisol $(CLr_{(F)-exo})$, two independent parameters.

$$CL_{m(6\beta)-exo} = \qquad [2]$$

$$\frac{X_{(6\beta)-exo}}{AUC_{(F)-exo}} = \left(\frac{X_{(F)-exo}}{AUC_{(F)-exo}}\right)\left(\frac{X_{(6\beta)-exo}}{X_{(F)-exo}}\right) = CL_{r(F)-exo}\left(\frac{X_{(6\beta)-exo}}{X_{(F)-exo}}\right)$$

That is, the urinary 6β-hydroxycortisol/cortisol ratio $(=X_{(6\beta)-exo}/X^{(F)-exo})$ can be expressed as:

$$6\beta-\text{hydroxycortisol/cortisol} = \frac{CL_{m(6\beta)-exo}}{CL_{r(F)-exo}} \qquad [3]$$

This means that the urinary 6β-hydroxycortisol/cortisol ratio is valid as the index only in the case of no intra- and inter-individual variabilities in the renal clearance of cortisol $(CLr_{(F)-exo})$. However, approximately 5-fold interindividual variability was observed in the renal clearance ($CLr_{(F)-exo}$; 2.23 ml/min for Subject A, 0.45 ml/min for Subject B, and 0.75 ml/min for Subject C) (Table I) after administrating labeled cortisol to these three subjects. Furthermore, the intraindividual variabilities of the renal clearance at 2-h (or 4-h) intervals from 10:00 to 16:00 (18:00) were 4.6-fold from 0.62 to 2.85 ml/min for Subject A, 3.6-fold from 0.17 to 0.61 ml/min for Subject B, and 2.1-fold from 0.40 to 0.82 ml/min for Subject C (Table I). It is obvious that the urinary 6β-hydroxycortisol/cortisol ratio varied with the renal clearance of cortisol, which indicates that the urinary ratio of "endogenous 6β-hydroxycortisol to cortisol" as a conventional index does not always reflect accurately in vivo CYP3A activity.

(2) Evaluation of Urinary Ratio of Endogenous 6β-Hydroxycortisol/Cortisol as a Conventional Index for In Vivo CYP3A Phenotyping: (Comparative Example)

Figure 2:
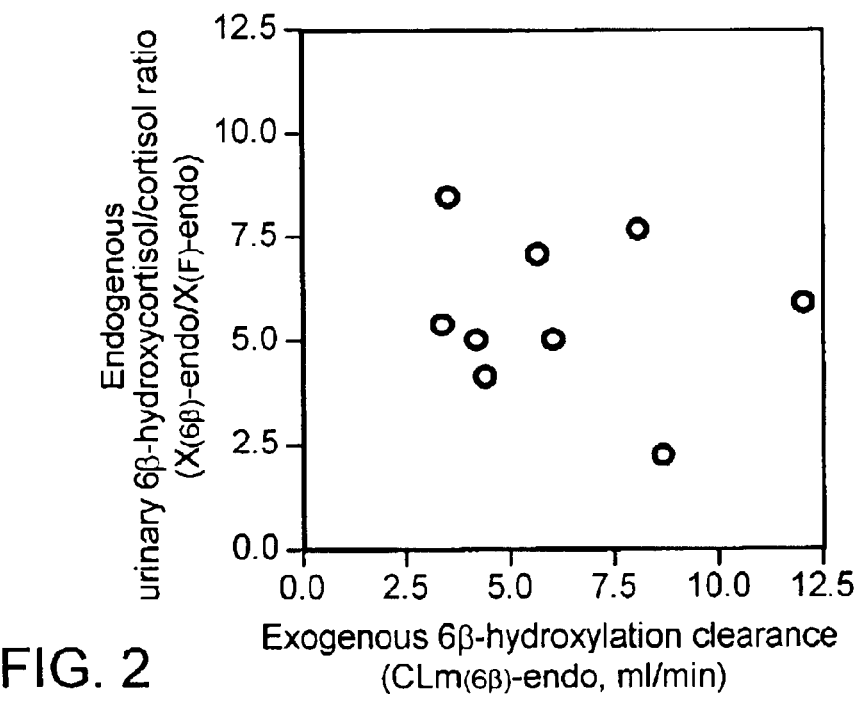
FIG. 2 illustrates the relationship between urinary ratio of endogenous 6β-hydroxycortisol to cortisol (=$X_{(6\beta)-endo}/X_{(F)-endo}$) versus exogenous metabolic clearance ($CLm_{(6\beta)-exo}$) for the 6β-hydroxylation of cortisol after administrating stable isotopically labeled cortisol to three subjects, showing no correlation between $X_{(6\beta)-endo}/X_{(F)-endo}$ and $CLm_{(6\beta)-exo}$ obtained at timed periods of 10:00–12:00, 12:00–14:00, and 14:00–16:00 for Subjects A and C and of 10:00–12:00, 12:00–14:00, and 14:00–18:00 for Subject B.

The validity of the urinary ratio of "endogenous 6β-hydroxycortisol/cortisol ($X_{(6\beta)-endo}/X_{(F)-endo}$)," which has been used as a non-invasive index for in vivo CYP3A phenotyping, was then evaluated by examining the correlation with the 6β-hydroxylation clearance of exogenous (labeled) cortisol ($CLm_{(6\beta)-exo}$). abscissa/ordinate of FIG. 2

In FIG. 2, the abscissa is fractional metabolic clearance for the 6β-hydroxylation of exogenous (labeled) cortisol ($CLm_{(6\beta)-exo}$) as a reliable index to show CYP3A activity. The ordinate of FIG. 2 is endogenous 6β-hydroxycortisol/cortisol ratio (=$X_{(6\beta)-endo}/X_{(F)-endo}$) in urine. The values are reviewed if they are reliable as an index for CYP3A activity by examining the correlation with abscissa, $CLm_{(6\beta)-exo}$. In FIG. 2, the values for the plots of $CLm_{(6\beta)-exo}$ (abscissa: ml/min) versus $X_{(6\beta)-endo}/X_{(F)-endo}$ (ordinate) are; (8.69:2.18), (8.11:7.63), and (12.0:5.81) for Subject A; (4.22:4.98), (3.57:8.44), and (3.39:5.35) for Subject B; and (4.48:4.10), (5.66:7.05), and (6.10:5.02) for Subject C, which were obtained at a time period (2-h intervals) of 10:00–12:00, 12:00–14:00, and 14:00–16:00 for Subjects A and C and of 10:00–12:00, 12:00–14:00, and 14:00–18:00 for Subject B. Endogenous cortisol and 6β-hydroxycortisol were determined by mass spectrometry simultaneously with their exogenous labeled counterparts for examining the relationship between exogenous $CLm_{(6\beta)-exo}$ versus endogenous $X_{(6\beta)-endo}/X_{(F)-endo}$.

As shown in FIG. 2, there was no correlation between the endogenous 6β-hydroxycortisol/cortisol ratio and the exogenous metabolic clearance. It is concluded that the endogenous 6β-hydroxycortisol/cortisol ratio as a conventional index is not appropriate for phenotyping in vivo CYP3A activity in human.

(3) Evaluation of Metabolic Clearance for the 6β-Hydroxylation of Endogenous Cortisol as an Index for In Vivo Human CYP3A Phenotyping: (Example) Abscissa/Ordinate of FIG. 1

In FIG. 1, the abscissa is fractional metabolic clearance for the 6β-hydroxylation of exogenous (labeled) cortisol ($CLm_{(6\beta)-exo}$) as described in the Comparative Example above, and the ordinate is endogenous metabolic clearance ($CLm_{(6\beta)-endo}$) which is considered to be involved in the process of adrenal cortisol secretion. The values for the plots of $CLm_{(6\beta)-exo}$ (abscissa: ml/min) versus $CLm_{(6\beta)-endo}$ (ordinate: ml/min) are; (8.69:3.78), (8.11:3.09), and (12.0:1.70) for Subject A; (4.22:2.16), (3.57:1.37), and (3.39:1.57) for Subject B; and (4.48:2.99), (5.66:1.84), and (6.10:1.87) for Subject C, which were obtained at a timed period (2 h-intervals) of 10:00–12:00, 12:00–14:00, and 14:00–16:00 for Subjects A and C and of 10:00–12:00, 12:00–14:00, and 14:00–18:00 for Subject B. Endogenous cortisol and 6β-hydroxycortisol were determined by mass spectrometry simultaneously with their exogenous labeled counterparts for examining the relationship between exogenous $CLm_{(6\beta)-exo}$ versus endogenous $CLm_{(6\beta)-endo}$.

The 6β-hydroxylation of endogenous cortisol was estimated as "endogenous metabolic clearance ($CLm_{(6\beta)-endo}$)" by using the following equation:

$$CLm_{(6\beta)-endo} = X_{(6\beta)-endo}/AUC_{(F)-endo} \quad [4]$$

In a test period of 6 h or 8 h after administrating labeled cortisol to three subjects, the values for endogenous 6β-hydroxylation clearance ($CLm_{(6\beta)-endo}$) were 2.94 ml/min from 10:00 to 16:00 (Subject A), 1.69 ml/min from 10:00 to 18:00 (Subject B), and 2.25 ml/min from 10:00 to 16:00 (Subject C), respectively. The exogenous $CLm_{(6\beta)-exo}$ values at the same period were 8.77 ml/min (Subject A), 3.94 ml/min (Subject B), and 4.75 ml/min (Subject C) as shown in Table I. The value for endogenous clearance ($CLm_{(6\beta)-endo}$) was lower than that of the exogenous clearance ($CLm_{(6\beta)-exo}$) in each subject because of the influence of the adrenal secretion of endogenous cortisol. There was, however, a good correlation between the endogenous and exogenous metabolic clearances (r=0.7733, P<0.005) at a timed period (2 h-intervals) from 10:00 to 16:00 (18:00) (FIG. 1). A prolonged sampling interval of 4 h or 6 h gave a higher correlation between the endogenous and exogenous metabolic clearances (r=0.9022, P<0.005 for 4 h-intervals and r=0.9521, P<0.005 for 6 h-intervals). These results imply that the endogenous metabolic (6β-hydroxylation) clearance can be used as an appropriate index for in vivo CYP3A phenotyping.

For the last two decades, the endogenous 6β-hydroxycortisol/cortisol ratio in urine has been considered to be valid for evaluating CYP3A metabolic capacities, since the 24-h urinary 6β-hydroxycortisol/cortisol ratio, with no significant day-to-day intraindividual variations, can be changed by CYP3A inducers or inhibitors. It is well known that the secretory pattern of cortisol in normal man is comprised of seven or more major episodes throughout the day, large elevations of the plasma cortisol occurring in the early morning hours followed by a series of smaller elevations in the daytime. The amount of endogenous 6β-hydroxycortisol excreted in urine also increases with an increase in that of urinary cortisol excreted under the influence of adrenal cortisol secretion. The apparently synchronized excretions of cortisol and 6β-hydroxycortisol in urine have led to the wrong idea that the production of 6β-hydroxycortisol catalyzed by CYP3A isozyme can be expressed as the ratio 6β-hydroxycortisol/cortisol in urine, in order to adjust for day-to-day or within-day variation in adrenal cortisol secretion. It should be noted that the urinary ratio (6β-hydroxycortisol/cortisol) is valid as the index for in vivo CYP3A activity only when the renal clearance ($CLr_{(F)}$) of cortisol does not largely vary. That is, the urinary ratio can be changed by CYP3A inducers or inhibitors only when the change of 6β-hydroxylation clearance ($CLm_{(6\beta)}$) by induction or inhibition is much larger than the magnitude of variability in the renal clearance ($CLr_{(F)}$) (see Equation 3). Of course, the urinary 6β-hydroxycortisol/cortisol ratio cannot be a measure of person-to-person differences in CYP3A activity owing to the interindividual variability of the renal clearance ($CLr_{(F)}$). The present method can precisely assess the in vivo CYP3A activity even when the intra- and interindividual variations in metabolic clearances catalyzed by enzymes other than CYP3A as well as in the renal clearance of cortisol exist.

(4) Application to the Evaluation of In Vivo CYP3A Activity After Administration of Macrolide Antibiotic Clarithromycin: (Example)

Administration of labeled cortisol and the simultaneous measurements of exogenous (labeled) and endogenous cortisol and 6β-hydroxycortisol provided evidence that metabolic clearance for the endogenous 6β-hydroxylation of cortisol is an appropriate index for in vivo CYP3A phenotyping. The proposed CYP3A-phenotyping was then assessed by examining the inhibitory effects of a macrolide antibiotic clarithromycin on the in vivo CYP3A activity. Macrolide antibiotics generally form inactive iron-metabolite complexes with CYP3A and cause a decrease in its catalytic activity. The macrolide clarithromycin is a substrate and an inhibitor of CYP3A and considerably increases the plasma concentrations of clinically important CYP3A substrates.

a probe for CYP3A phenotyping, producing a 64% reduction in the systemic clearance of midazolam following pretreatment with 500-mg of clarithromycin twice a day for 7 days, resulting in a doubling of the midazolam sleep time (J. C. Gorski, et al., (1998) Clin. Pharmacol. Ther., 64, pp 133–143.). In the present method, inhibitory effects of clarithromycin on the in vivo CYP3A activity were well evaluated, as evident by the decrease of approximately 50% in the endogenous 6β-hydroxylation clearance ($CLm_{(6\beta)\text{-}endo}$) during treatment with 200-mg of clarithromycin twice a day for 6 days. The present method requires no probe drugs for administration, providing a real-time enzyme activity in vivo as shown in FIG. 3.

(5) General Procedures:

a) Collections of Blood and Urine Samples for the CYP3A Phenotyping in Humans: A timed urine collection and blood sampling during a period of the urine collection

TABLE II

| Clock time | Day 0 (Predose) | Day 1 | Day 2 | Day 3 | Day 4 | Day 5 | Day 6 | Day 13 | Day 68 |
|---|---|---|---|---|---|---|---|---|---|
| 10:00~12:00 | 3.61 | 3.71 | | | 1.71 | | 1.72 | 3.44 | 3.38 |
| 12:00~14:00 | 3.57 | 2.45 | 1.53[A] | 1.58[A] | 1.73 | 1.32[A] | 1.29 | 2.56 | 3.37 |
| 14:00~16:00 | 3.36 | 2.18 | | | 1.67 | | 1.52 | 2.88 | 3.27 |
| 16:00~18:00 | 3.85 | 2.04 | 1.75 | 1.63 | 1.99 | 1.44 | 1.46 | 2.60 | 3.46 |
| 18:00~20:00 | 2.97 | 1.83 | 1.80 | 1.80 | 1.58 | 1.94 | 1.31 | 2.79 | 3.93 |
| Mean ± SD | 3.47 ± 0.33 | 2.44 ± 0.74 | 1.69 ± 0.14 | 1.67 ± 0.12 | 1.74 ± 0.15 | 1.57 ± 0.33 | 1.46 ± 0.18 | 2.85 ± 0.35 | 3.48 ± 0.26 |

[A]10:00~16:00

One healthy male volunteer (Subject D; 25 years old) received 200-mg of clarithromycin every 12 hr at 10:00 and 22:00 for 6 days. The subject was not receiving any medication. Blood samples (1 or 2 ml each) were obtained at 0.5- or 1.0-hour intervals from 10:00 to 20:00 (22:00) on days 0 (predose), 1, 4, 6, 13 and 68 after dosing clarithromycin at 10:00 a.m. On days 2, 3 and 5, blood samples were obtained every 2 hr after dosing clarithromycin (10:00 to 20:00). Urine samples were obtained at a timed period (0–2, 2–4, 4–6, 6–8, 8–10, and 10–12) and the volume of the urine samples was noted. The recommended frequency of blood sampling is at least one time during a 2-hour urine collection. Urinary concentrations of cortisol and 6β-hydroxycortisol and plasma concentrations of cortisol were determined by HPLC and GC-MS, respectively. "The endogenous metabolic clearance ($CLm_{(6\beta)\text{-}endo}$)" was calculated by Equation 4. As shown in Table II, the $CLm_{(6\beta)\text{-}endo}$ value was 3.47±0.33 ml/min (mean±SD) on the day before clarithromycin administration (day 0). The $CLm_{(6\beta)\text{-}endo}$ value rapidly decreased from 3.71 ml/min to 1.83 ml/min by the initial administration of 200-mg of clarithromycin at 10:00 a.m. on day 1 (Table II). The $CLm_{(6\beta)\text{-}endo}$ values then varied only 1.2-fold from 1.46 ml/min to 1.74 ml/min during treatment with clarithromycin (days 2–6), producing 50–58% reduction in 6β-hydroxylation clearance (FIG. 3). After termination of the administration, the values increased to 2.85±0.35 ml/min after a 7-day washout period (day 13) and 3.48±0.26 ml/min after a 2-month washout period (day 68), respectively. Inhibitory effects of clarithromycin on the 6β-hydroxylation clearance were clearly detected. On the other hand, inhibition of the in vivo CYP3A activity by treatment with clarithromycin through days 1 to 6 could not be well evaluated by the conventional CYP3A phenotyping using the urinary 6β-hydroxycortisol/cortisol ratio as an index (FIG. 4).

According to the past literature references, clarithromycin significantly altered the pharmacokinetics of midazolam as (e.g., 2-hour) are required. An aliquot of blood is collected using standard venipuncture technique. Only one milliliter of blood is required for analysis. The frequency of blood sampling is at least one time during a 2-hour urine collection. The heparinized blood is collected in glass tubes and centrifuged, and the plasma is kept frozen at −20° C. until analysis. The urine sample is collected using a standard urine collection bottle. Each of the urine collection periods is started by asking the subjects to empty their urinary bladders. At least 2-hour urine collection is recommended. Only one milliliter of urine is required for analysis. The volume of the urine samples is noted. The sample is stored at −20° C. until analysis. A period of less than 2-hour for the urine collection may be possible, if one empties his or her urinary bladder completely enough to determine the accurate amounts of 6β-hydroxycortisol excreted in the urine, at the point of starting and terminating the urine collection. It should be noted that a prolonged urine sampling period provides a higher accuracy in determining metabolic clearance for the 6β-hydroxylation of endogenous cortisol, as described in the "Example" of

DETAILED DESCRIPTION OF THE INVENTION b) Measurements of Plasma Cortisol and Urinary 6β-Hydroxycortisol: Plasma concentrations of cortisol and urinary amounts of 6β-hydroxycortisol can be determined by several established methods, including HPLC, GC-MS, radioimmunoassay (RIA), and enzyme immunoassay. The HPLC and GC-MS techniques offer the advantages of sensitively and selectively analyzing these compounds. A typical procedure for the HPLC assays of cortisol and 6β-hydroxycortisol in urine, developed for this invention, is briefly described as follows:

The HPLC separations are performed on a reversed-phase column, monitored by UV absorbance at 239 nm and operated at 0.8 ml/min using following gradient of solvent mixtures (A) 0.05M $KH_2PO_4$-0.01M $CH_3COOH$ (pH 3.77) and (B) 0.05M $KH_2PO_4$-0.01M $CH_3COOH$:acetonitrile (4:6, vol/vol). Extraction procedures employed for the HPLC analyses of cortisol and 6β-hydroxycortisol in urine are performed according to the previously reported procedures (J. Lykkesfeldt, et al., (1994) J. Chromatogr. B., 660, pp23–29.). Methylprednisolone can be used as the analytical internal standard. Peak areas of cortisol, 6β-hydroxycortisol, and methylprednisolone are measured. Precision values (relative standard deviations) were all below 6.63% for cortisol and 6β-hydroxycortisol, and accuracy (relative error) was +0.46% for cortisol and +0.27% for 6β-hydroxycortisol, respectively, in the investigated urine samples.

c) The fractional metabolic clearance for the 6β-hydroxylation of endogenous cortisol ($CLm_{(6β)}$) is expressed as the amount of urinary excreted 6β-hydroxycortisol ($X_{(6β)}$) divided by the area under the concentration-time curve of cortisol ($AUC_{(F)}$); that is, $CLm_{(6β)}=X_{(6β)}/AUC_{(F)}$.

The 6β-hydroxylation clearance ($CLm_{(6β)}$) also is expressed in the forms of the following equation: $CLm_{(6β)}=x_{(6β)/c(F)}$, wherein $x_{(6β)}$ is the mean excretion rate of 6β-hydroxycortisol in a period of the urine collection, and $c_{(F)}$ is the plasma concentration of cortisol at a midpoint of the urine collection period.

This invention is first undertaken to determine fractional metabolic clearance specific for the 6β-hydroxylation of cortisol by administrating stable isotopically labeled cortisol to human subjects in order to accurately evaluate the in vivo cytochrome P450 3A (CYP3A) activities. The approach provides a new and reliable index for CYP3A phenotyping in humans using endogenous metabolic clearance for the 6β-hydroxylation of cortisol. The method is minimally invasive, requiring at least a 2 hr-urine collection and one blood sample to know actual and real-time enzyme activity. This is the safest and simplest of all phenotyping procedures since administration of a probe drug is not required. The invention also offers an efficient CYP3A phenotyping without high laboratory cost, and is useful for predicting or assessing individual drug disposition in various patients and for identifying individuals with important genetic variants affecting CYP3A activity, in the fields of drug development and clinical research and practice.

While the new methods have been described in detail with particular references to the preferred embodiments thereof, it should be understood that many modifications, additions and deletions may be made thereto without departure from the spirit and scope of the inventive method as set forth in the following claims.

What is claimed is:

1. A method for evaluating the level of in vivo CYP3A activity to metabolize CYP3A substrate substances of a subject by measuring metabolic clearance for the 6β-hydroxylation of cortisol in said subject as an index for said in vivo CYP3A activity without use of labeled exogenous cortisol, wherein the method comprises the steps of:

(a) collecting urine sample of said subject accumulated in a urine collection period and obtaining a blood sample of said subject at least once during said urine collection period;

(b) measuring the cortisol concentration in plasma or serum of said blood sample or samples and calculating the area under the plasma or serum concentration-time curve of cortisol ($AUC_{(F)}$) of said urine collection period;

(c) measuring the volume and the 6β-hydroxycortisol concentration of said urine sample to determine the total amount (X(6β)) of 6β-hydroxycortisol excreted in the urine during said urine collection period;

(d) calculating the metabolic clearance ($CLm(6β)=X(6β)/AUC_{(F)}$) for the 6β-hydroxylation of cortisol as an index of in vivo CYP3activity of said subject at the time when said measurements are made.

2. A method of claim 1 wherein said urine collection period is at least 2-hours.

3. A method for evaluating the level of in vivo CYP3A activity to metabolize CYP3A substrate substances in a subject by measuring metabolic clearance for the 6β-hydroxylation of cortisol as an index for said in vivo CYP3A activity without use of labeled exogenous cortisol wherein the method comprises the steps of:

(a) obtaining urine sample accumulated in a urine collection period and blood sample obtained at a midpoint of said urine collection period from said subject;

(b) measuring the cortisol concentration ($c_{(F)}$) in plasma or serum of said blood sample at the midpoint of said urine collection period;

(c) measuring the volume and the 6β-hydroxycortisol concentration of said urine sample to calculate the mean excretion rate of 6β-hydroxycortisol in the urine (x(6β)) of said urine collection period; and (d) calculating the metabolic clearance for the 6β-hydroxylation of cortisol ($CLm(6β)=x(6β)/c_{(F)}$) as an index of in vivo CYP3A activity of said subject at the time when said measurements are made.

4. A method of claim 3 wherein said urine collection period is at least 2-hours.

5. A method for determining the amount of CYP3A substrate drug to be administered to a subject, wherein the method comprises the steps of:

(a) collecting urine sample of said subject accumulated in a urine collection period and obtaining a blood sample of said subject at least once during said urine collection period;

(b) measuring the cortisol concentration in plasma or serum of said blood sample or samples and calculating the area under the plasma or serum concentration-time curve of cortisol ($AUC_{(F)}$) of said urine collection period;

(c) measuring the volume And the 6β-hydroxycortisol concentration of said urine sample to determine the total amount (X(6β)) of 6β-hydroxycortisol excreted in the urine during said urine collection period;

(d) calculating the metabolic clearance ($CLm(6β)=X(6β)/AUC_{(F)}$) for the 6β-hydroxylation of cortisol as an index of in vivo CYP3A activity of said subject at the time when said measurements are made; and (e) comparing the calculated metabolic clearance for the 6β-hydroxylation of endogenous cortisol in said subject with reference values to decide the amount of said drug to be administered.

6. A method of claim 5 wherein said reference values are metabolic clearance values for the 6β-hydroxylation of endogenous cortisol in other subject.

7. A method of claim 5 wherein said reference values are metabolic clearance values for the 6β-hydroxylation of endogenous cortisol previously determined in said subject.

8. A method for determining the amount of a CYP3A substrate drug to be administered to a subject, wherein the method comprises the steps of;

(a) obtaining urine sample accumulated in a urine collection period and blood sample obtained at a midpoint of said urine collection period from said subject;

(b) measuring the cortisol concentration ($c_{(F)}$) in plasma or serum of said blood sample at the midpoint of said urine collection period;

(c) measuring the volume and the 6β-hydroxycortisol concentration of said urine sample to calculate the mean excretion rate of 6β-hydroxycortisol in the urine ($x(6\beta)$) of said urine collection period;

(d) calculating the metabolic clearance for the 6β-hydroxylation of cortisol ($CLm(6\beta)=x(6\beta)/c_{(F)}$ as an index of in vivo CYP3A activity of said subject at the time when said measurements are made; and (e) comparing said calculated metabolic clearance for the 6β-hydroxylation of endogenous cortisol in said subject with reference values to decide the amount of said drug to be administered.

9. A method of claim 8 wherein said reference values are metabolic clearance values for the 6β-hydroxylation of endogenous cortisol in other subjects.

10. A method of claim 8 wherein said reference values are metabolic clearance values for the 6β-hydroxylation of endogenous cortisol previously determined in said subject.

11. A method for evaluating influence of a drug or a drug candidate on the CYP3A activity, wherein the method comprises the steps of:

(a) administering said drug or drug candidate to a subject, (b) collecting urine sample of said subject accumulated in a urine collect period and obtaining a blood sample of said subject at least once during said urine collection period;

(c) measuring the cortisol concentration in plasma or serum of said blood sample or samples and calculating the area under the plasma or serum concentration-time curve of cortisol ($AUC_{(F)}$) of said urine collection period;

(d) measuring the volume and the 6βhydroxycortisol concentration of said urine sample to determine the total amount ($X(6\beta)$) of 6βhydroxycortisol excreted in the urine during said urine collection period;

(e) calculating the metabolic clearance ($CLm(6\beta)=X(6\beta)/AUC_{(F)}$) for the 6β-hydroxylation of cortisol as an index of in vivo CYP3A activity of said subject at the time when said measurements are made;

(f) comparing said calculated metabolic clearance for the 6β-hydroxylation of endogenous cortisol in said subject with a value of metabolic clearance of the 6β-hydroxylation of endogenous cortisol of said subject determined in accordance with the steps (b) to (e) without administration of said drug or drug candidate, and judging said drug or drug candidate as having influence on the CYP3A activity when there is difference between the values.

12. A method for evaluating influence of a drug or a drug candidate on the CYP3A activity, wherein the method comprises the steps of:

(a) administering said drug or drug candidate to a subject, (b) obtaining urine sample accumulated in a urine collection period and blood sample obtained at a midpoint of said urine collection period from said subject;

(c) measuring the cortisol concentration ($c_{(F)}$) in plasma or serum of said blood sample at the midpoint of said urine collection period;

(d) measuring the volume and the 6β-hydroxycortisol concentration of said urine sample to calculate the mean excretion rate of 6β-hydroxycortisol in the urine ($x(6\beta)$) of said urine collection period;

(e) calculating the metabolic clearance for the 6β-hydroxylation of cortisol ($CLm(6\beta)=x(6\beta)/c_{(F)}$) as an index of in vivo CYP3A activity of said subject at the time when said measurements are made; and (f) comparing said calculated metabolic clearance for the 6β-hydroxylation of endogenous cortisol in said subject with a value of metabolic clearance of the 6β-hydroxylation of endogenous cortisol of said subject determined in accordance with the steps (b) to (e) without administration of said drug or drug candidate, and judging said drug or drug candidate as having influence on the CYP3A activity when there is difference between the values.

* * * * *